(12) United States Patent
Szczykutowicz

(10) Patent No.: US 10,964,074 B2
(45) Date of Patent: Mar. 30, 2021

(54) SYSTEM FOR HARMONIZING MEDICAL IMAGE PRESENTATION

(71) Applicant: Wisconsin Alumni Research Foundation, Madison, WI (US)

(72) Inventor: Timothy Szczykutowicz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 130 days.

(21) Appl. No.: 16/259,073

(22) Filed: Jan. 28, 2019

(65) Prior Publication Data

US 2020/0242815 A1 Jul. 30, 2020

(51) Int. Cl.
| | |
|---|---|
| *G06T 11/00* | (2006.01) |
| *A61B 6/00* | (2006.01) |
| *G16H 30/20* | (2018.01) |
| *G06T 7/00* | (2017.01) |
| *G06F 16/583* | (2019.01) |
| *A61B 6/03* | (2006.01) |
| *G16H 30/40* | (2018.01) |

(52) U.S. Cl.
CPC .......... *G06T 11/005* (2013.01); *A61B 6/5205* (2013.01); *A61B 6/5294* (2013.01); *G06F 16/583* (2019.01); *G06T 7/0012* (2013.01); *G16H 30/20* (2018.01); *A61B 6/032* (2013.01); *A61B 6/037* (2013.01); *A61B 6/563* (2013.01); *G06T 2207/30004* (2013.01); *G16H 30/40* (2018.01)

(58) Field of Classification Search
CPC ....... G06T 5/00; G06T 7/0012; G06T 11/005; G06T 5/003; G06T 5/10; G06T 5/20; G06T 7/0014; G06T 11/008; G06T 2207/10104; G06F 17/30247
USPC .............................. 382/131, 128, 47; 378/19
See application file for complete search history.

(56) References Cited

U.S. PATENT DOCUMENTS

| | | | |
|---|---|---|---|
| 6,904,161 | B1 | 6/2005 | Becker et al. |
| 7,787,672 | B2 | 8/2010 | Reicher et al. |
| 9,842,413 | B2 | 12/2017 | Kaftan et al. |
| 2009/0219289 | A1 | 9/2009 | Kalvin |
| 2010/0322497 | A1 | 12/2010 | Dempsey et al. |

(Continued)

FOREIGN PATENT DOCUMENTS

| | | |
|---|---|---|
| EP | 2791838 A2 | 10/2014 |
| KR | 20160089194 A | 7/2016 |

OTHER PUBLICATIONS

International Search Report for App.No. PCT/US2020/012037.
(Continued)

*Primary Examiner* — Phuoc H Doan
(74) *Attorney, Agent, or Firm* — Boyle Fredrickson, S.C.

(57) ABSTRACT

A system for processing medical image data stores high information content volumetric (HICV) data reconstructed from different medical imaging devices. Images normally requiring differing image imaging parameters can instead be created by processing of the HICV data, importantly without access to the original reconstruction algorithms or machine. The invention also allows different medical images to be harmonized for ready comparison or according to a desired image sequence for particular diagnostic purpose without any need to rescan the patient or to enforce cumbersome universal protocol standards.

18 Claims, 5 Drawing Sheets

(56) References Cited

U.S. PATENT DOCUMENTS

2012/0275675 A1    11/2012  Piron et al.
2014/0369577 A1*   12/2014  Collins .................. A61B 6/563
                                                         382/128
2015/0356754 A1*   12/2015  Kaftan .................. G06T 11/008
                                                         382/131

OTHER PUBLICATIONS

Choe et al.; "Deep Learning-based Image Conversion of CT Reconstruction Kernels Improves Radiomics Reproducibility for Pulmonary Nodules or Masses." radiology.rsna.org; Radiology: vol. 292: No. 2; pp. 365-373 (Aug. 2019).

Wilberger et al.; "Spatial domain image filtering in computed tomography: feasibility study in pulmonary embolism." European radiology 13, No. 4, pp. 717-723 (2003).

Ohkubo et al. "Image filtering as an alternative to the application of a different reconstruction kernel in CT imaging: feasibility study in lung cancer screening." Medical physics 38, No. 7, pp. 3915-3923 (Jul. 2011).

Lapp et al.; "Interactively variable isotopic resolution in computed tomography." Physics in Medicine & Biology 53, No. 10: pp. 2693-2713 (2008) UK.

Weiss et al.; "Hybrid convolution kernel: optimized CT of the head, neck, and spine." American Journal of Roentgenology 196, No. 2; pp. 403-406; (Feb. 2011).

Lee et al.; "CT image conversion among different reconstruction kernels without a sinogram by using a convolutional neural network." Korean journal of radiology 20, No. 2; pp. 295-303; (Apr. 2018) KR.

* cited by examiner

SYSTEM FOR HARMONIZING MEDICAL IMAGE PRESENTATION

STATEMENT REGARDING FEDERALLY SPONSORED RESEARCH OR DEVELOPMENT

—

CROSS REFERENCE TO RELATED APPLICATION

—

BACKGROUND OF THE INVENTION

Medical imaging has advanced from a single modality of planar x-rays to a wide variety of computer-assisted imaging techniques included computed tomography (CT), magnetic resonance imaging (MRI), single photon emission computed tomography (SPECT), positron emission tomography (PET), and the like.

Generally, each of these medical imaging modalities measures physical properties of a volume of tissue in a patient to obtain "acquisition data". This acquisition data is normally unintelligible as acquired but may be "reconstructed" to produce a volume of voxel data generally corresponding the volume of the patient being scanned. That is, each voxel of the volume of voxel data maps to a corresponding unique location within the patient volume.

The value of the voxel data will differ depending on the image modality. For example, with CT voxel data, the voxels indicate x-ray attenuation of the corresponding tissue volume. With MRI data, the voxels indicate measures of local magnetization properties of molecules of the corresponding tissue volumes. PET and SPECT voxel data indicates nuclear decay events occurring in the corresponding volume of tissue.

The three-dimensional voxel data may be displayed as a series of two-dimensional "slice" images with voxel values mapped to brightness or color or by similar two-dimensional projections of the 3D data (for example, as a rotatable 3D model viewable in two dimensions or in a time series of two-dimensional images). As used herein, "two-dimensional" refers generally to images displayable on a computer display or the like for human viewing.

The reconstruction process applies a sophisticated mathematical algorithm to the acquisition data to produce the volumetric data. In a CT reconstruction, for example, the acquisition data may represent xray attenuation edgewise through an image slice at various angles around the slice. The reconstruction process converts this edgewise view into a cross-sectional view separating the attenuation of individual volumes within the slice that are only seen in combination in the edgewise view. CT reconstruction may use techniques such as forward/backward projection reconstruction, Fourier transform reconstruction, etc.

An equally sophisticated reconstruction algorithm is used with MRI data. Here the acquisition data represents the time domain radiofrequency signal of nuclear resonances in patient tissue during the application of different gradient magnetic fields to the patient. The reconstruction processes a set of these time domain radiofrequency signals into voxel data, for example, using a two-dimensional Fourier transform. The reconstruction algorithm may also handle: partitioning of the volumetric data into individual slice images, adjustments for patient variations, and accommodation of image artifacts (for example, from radiopaque fixtures holding, or hardware embedded in, the patient). The reconstruction algorithm may receive a variety of imaging parameters from the user for the purpose of setting image resolution and acquisition conditions, for example, in CT, setting the x-ray energy and tube current.

The reconstruction algorithm is closely tied to the hardware of the medical imaging device (a built-in reconstruction "engine") and normally tuned to work with that specific imaging device hardware. In part, this is because many of the imaging parameters needed for reconstruction are unique to the physical properties and capabilities of the imaging device (e.g., the size and number of x-ray sensors in a CT machine). In addition, the reconstruction algorithms often incorporate multiple correction factors into the reconstruction process to address manufacturing limitations in a given model or even a given imaging machine of a model series. For example, a CT reconstruction engine may perform not only back projection (discussed above) but correction factors for x-ray sensor manufacturing variation, alignment variation, x-ray tube aging, machine operating temperature, flexure in the gantry with rotation, etc.

For this reason reconstruction engines between different manufacturers and even between different model years from an individual manufacture may be incompatible. As a result, the process of converting from acquisition data to volumetric data acquired by a given medical imaging device normally requires access to the reconstruction engine on that medical device performing the image acquisition.

Before scanning a patient on a medical imaging device, the device operator and/or physician agree upon a set of imaging parameters including, for example, the volume of the patient to be imaged (e.g., a liver study), an orientation of the desired images (e.g., sagittal, coronal etc.) together with details about desired resolution (e.g., voxel size), filtration, and machine operation (e.g., for example, x-ray energy, tube current, etc. in a CT device). Images are then produced according to those imaging parameters.

The particular parameter selected by the device operator, or even a physician, may differ from those required by the reviewing radiologist. For example, the radiologist may prefer different view orientations or different sets of view orientations, or different filtration. Often, imaging parameters selected for a particular study are unsuitable to address a subsequent diagnostic question requiring a new scan to be conducted. When longitudinal comparisons between studies on the same patient at different times must be conducted, variations in imaging parameters can make this comparison process difficult or impossible.

US patent application 2014/0369577 describes a system that addresses some of these problems of mismatch in the reconstruction used in the acquisition of data and the imaging parameters preferred or required by the reviewing radiologist. US patent application 2014/0369577 describes a system allowing two-way communication between the reviewing radiologist and the reconstruction engine of the medical imaging device, allowing the reviewing radiologist to iteratively vary the imaging parameters to obtain images according to his or her preference.

This solution has two drawbacks. First, there is no standard for such two-way communication among different manufacturers, and such devices providing two-way communication are not common even from a single manufacturer. For this reason, this approach would be unlikely to be practically workable in current healthcare facilities having multiple medical imaging devices from different manufacturers that are aware scans have been obtained from a remote facility. Individual cross sectional scanning modalities can easily have hundreds of protocols each with dozens of imaging parameters making device side management of these parameters difficult.

This approach contemplates that templates can be saved by the reviewing radiologist capturing his or her preferences (derived iteratively in communication with the reconstruction engine) for future use. Given the great variety in reconstruction engines and parameters, a large number of templates would be required associated not only with each type of study but also with each type of machine and its unique reconstruction engine configuration.

SUMMARY OF THE INVENTION

The present inventor has recognized that significant medical image features normally adjusted during reconstruction can in fact be adjusted after reconstruction eliminating the need to have access to the reconstruction engine of the medical imaging device. This ability to adjust the images after reconstruction is possible by performing an initial reconstruction to produce "high information content volumetric data" (HICV data) in lieu of the normal diagnostic images normally produced. HICV data is normally diagnostically inferior to image data produced by a reconstruction engine for a human diagnostician; nevertheless, HICV data can be stored once and later used to produce a wide range of different types of diagnostic quality images comparable to those produced by reconstruction engines.

The invention works with a variety of existing and anticipated medical imaging devices without access to those medical imaging devices during image manipulation. Most current medical imaging devices can be programmed with a template to produce the necessary HICV data. The invention permits a simplified profile to be created for image manipulation, eliminating a large number of normal imaging parameters normally required in a template system. In cases where there are two different scans of the patient which need to be compared, the invention provides a way of imposing matching formatting on the images (view orientation, filtering, slice thickness, etc.) to simplify the comparison process.

Specifically then, one embodiment of the invention provides a medical image processing system for data acquired from a medical imaging device collecting acquisition data from patients that is reconstructed to provide volumetric data. The medical image processing system includes a memory system storing high information content volumetric (HICV data from multiple medical imaging devices after reconstruction of acquisition data acquired by the multiple medical imaging devices. A presentation processor operates to:

(a) receive first and second image format requests for volumetric data from a given medical imaging device;

(b) process HICV data corresponding to the volumetric data to provide a first set of two-dimensional images having a first slice orientation and/or first spatial filtration; and (c) process the HICV data to provide a second set of two-dimensional images having a second slice orientation and/or second spatial filtration where at least one of the first and second slice orientation or at least one of the first and second spatial filtration differ.

It is thus a feature of at least one embodiment of the invention to permit a single stored set of data to be used to reproduce images having a variety of different parameters (filtration, orientation) without requiring access to the reconstruction engine of the medical imaging machine originally acquiring the data.

The HICV data may be data obtained from the medical imaging devices using imaging parameters minimizing filtration of the volumetric data.

It is thus a feature of at least one embodiment of the invention to allow repeated use of patient scan data, for example, for different diagnostic purposes or to conform with physician preferences, without the need to access the original reconstruction engine of the diagnostic imaging machine. The invention recognizes that many features of reconstruction are simply selective reduction of the information from HICV data that can be reproduced after reconstruction by modification of HICV data.

It is another object of a feature of at least one embodiment of the invention to minimize data storage costs by storing HICV data in place of many different formats of images.

The HICV data may be obtained from the medical imaging devices uses a highest resolution of the medical imaging devices, and/or using imaging parameters that maximize the information content of HICV data, or, for example, before windowing of Fourier data underlying the HICV data, and/or disabling maximum intensity projection processing and image segmentation.

It is thus a feature of at least one embodiment of the invention to provide a system that can work with existing legacy and future contemplated medical imaging devices by selecting from existing imaging parameters to maximize the information of the stored volumetric data.

The image format requests may identify among multiple templates stored in the memory system, the templates describing the processing of the HICV data to produce a set of two-dimensional images according to an image format request.

It is thus a feature of at least one embodiment of the invention to permit rapid processing of the HICV data using templates identified to a particular physician or particular diagnostic purpose. These templates can be much simpler than templates necessary to hold all imaging parameters, for example, originally used to create the HICV data or for normal template-type control of medical imaging devices.

The multiple templates further specify maximum intensity projections and/or image segmentation operations.

It is thus a feature of at least one embodiment of the invention to provide modification of the HICV not only with respect to slice orientation and filtration but also other image processing steps often performed by the reconstruction engine of a particular medical imaging device.

The presentation processor may include a network interface for communicating with at least one display terminal for displaying two-dimensional images to a healthcare professional and for receiving commands through the display terminal from the healthcare professional to modify the processing of the given HICV data.

It is thus a feature of at least one embodiment of the invention to permit interactive modification of the HICV data by a physician to produce desired images.

The HICV data may include metadata identifying a medical imaging device, and the image format request identifies a script associated with a medical imaging device providing the HICV data, the script providing additional filtration information.

It is thus a feature of at least one embodiment of the invention to provide a method of compensating for differences between HICV data for different medical imaging devices, for example, caused by their maximum slice resolution, minimum filtration etc. This script may be separated from the templates to simplify the construction and minimize the storage costs of both.

The memory system may store at least one given machine two-dimensional image corresponding to the given HICV data but produced by the medical imaging device in a reconstruction different from the reconstruction producing the given HICV data; and the presentation processor may develop a script by determining a processing of the given HICV data that produces two-dimensional images matching the given machine two-dimensional image, with processing defining the script.

It is thus a feature of at least one embodiment of the invention to provide an automatic generation for use of HICV data.

The medical image processing system may further:

(d) process second HICV data to provide a third set of two-dimensional images having a third slice orientation and/or third spatial filtration;

(e) receive a command from a display terminal identifying the first set of two-dimensional images and a request to match the first set of two-dimensional images and third set of two-dimensional images; and (f) processes the second HICV data a according to the processing of the given HICV data used to produce the first set of two-dimensional images to provide a fourth set of two-dimensional images and transmit the same to the display terminal.

It is thus a feature of at least one embodiment of the invention to provide a system of generating matching longitudinal studies of the patient to simplify the comparison process, particularly when one study was done by a different healthcare professional or from a remote facility and has substantially different formatting. By using HICV data, matching image series can be easily created well after the scanning.

In cases where one image is not based on HICV data, the medical imaging processing system may still provide this matching by modifying the image based on HICV data. In this case the medical image processing system operates to:

(d) receive a third set of two-dimensional images not obtained from HICV data having a third slice orientation and/or third spatial filtration;

(e) receive a command from a display terminal to match the first set of two-dimensional images to the third set of two-dimensional images; and (f) process the given HICV data to provide a fourth set of two-dimensional images to have a third slice orientation and/or third spatial filtration and transmit the third set of two-dimensional images and fourth set of two-dimensional images to the display terminal.

Thus it is a feature of at least one embodiment of the invention to make use of HICV data for matching longitudinal images even when one image is not HICV based.

The two-dimensional images not obtained from HICV data may include metadata describing the third slice orientation and/or third spatial filtration and the step (f) reads the metadata to provide the processing of the given HICV data to provide the fourth set of two-dimensional images.

It is thus a feature of at least one embodiment of the invention to make use of image metadata for converting HICV derived images to match non-HICV images.

The HICV data may include first and second volumetric data having a difference selected from the group consisting of: different regions of the body and different acquisition parameters.

It is thus a feature of at least one embodiment of the invention to accommodate possible alternative HICV formulations that can be obtained by changing the region of interest of the scan by providing multiple scans of different region of interest sizes.

These particular objects and advantages may apply to only some embodiments falling within the claims and thus do not define the scope of the invention.

DETAILED DESCRIPTION OF THE PREFERRED EMBODIMENT

Figure 1:
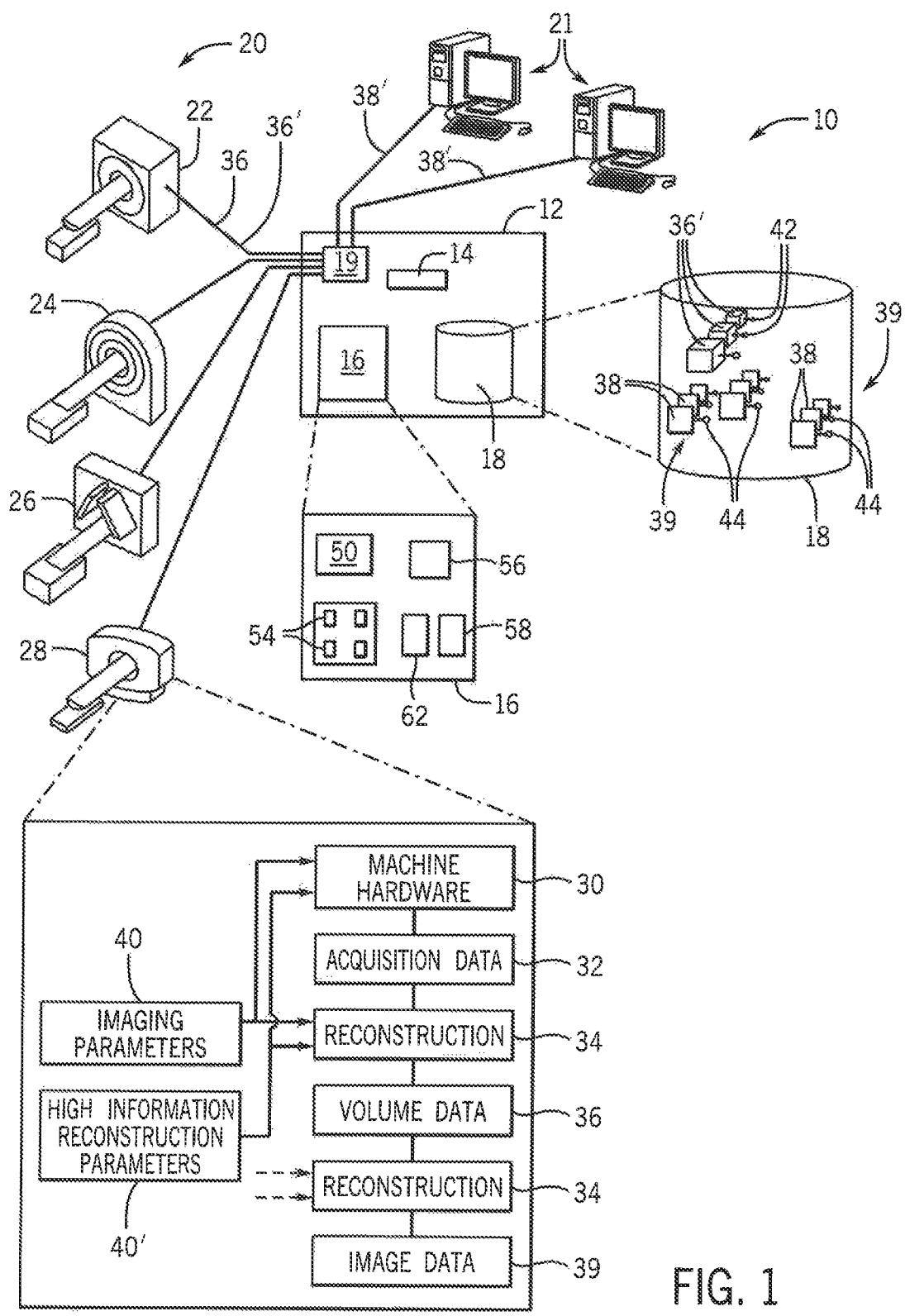
FIG. 1 is a block diagram of a system for harmonizing medical image presentation per the present invention showing multiple medical imaging devices each executing an image acquisition program including image reconstruction, the medical imaging devices communicating with a central presentation server providing images to display stations, the central presentation server including a memory for holding multiple programs including an image modification program as well as templates and conversion scripts, and providing a database for image data storage for high information content volumetric (HICV) data.

Referring now to FIG. 1, a medical image harmonizing system 10 per the present invention may provide for a presentation server 12 including an electronic processor 14 communicating with a memory 16 and a database 18. The presentation server 12 may provide for a standard general-purpose computer architecture used for data servers and the like.

In this regard, the presentation server 12 may provide for a network interface 19 communicating with multiple medical imaging machines 20, for example, the medical imaging machines 20 including but not limited to an MRI machine 22, a CT machine 24, a SPECT machine 26, and a PET machine 28, each of types well known in the art.

Each of these medical imaging machines 20 may provide for machine-specific acquisition software and hardware 30 for acquiring data from a volume of patient tissue of the patient being scanned by the particular medical imaging machine 20. That hardware 30 may include, for example, a rotating gantry with x-ray sensors and an x-ray tube in a CT machine 24 or set of gradient and readout coils and a polarizing magnet in an MRI machine 22 or various radiation detectors in the SPECT machine 26 or PET machine 28, also as understood in the art. The software 30 includes generally control software for controlling the mechanism of the medical imaging machine 20, and software and an electronic processor for processing the data acquired by the hardware and providing displays of images to a healthcare professional.

A scanning of a patient by the scanning hardware 30 of each of these types of medical imaging machines 20 results in a collection of acquisition data 32 related to a volume of a patient being scanned. The acquisition data 32 is normally in a form that is not useful for diagnosis and is not human readable. For example, in a CT machine, this acquisition data 32 may be in the form of multiple edgewise x-ray projections forming a sinogram or, in the case of an MRI machine, the acquisition data 32 may be a set of Fourier coefficients in so-called k-space.

The acquisition data 32 is received by a reconstruction engine 34 typically being specialized hardware and software unique to that particular machine. The reconstruction engine 34 operates to convert the acquisition data 32 into volumetric data 36 which is used internally (with further processing by the reconstruction engine 34) to produce image set 39, the latter typically being a series or stack of planar or two-dimensional images 38 (shown in FIG. 2) together covering the volume that was scanned.

The machine software and hardware 30 including the reconstruction engine 34 may receive imaging parameters 40, for example, from a healthcare professional operating the medical imaging machine 20, describing data needed for the reconstruction including, for example, slice thickness (being the volume thickness represented by a particular image 38), filtration (being a spatial filtration improving image readability), and orientation (describing the orientation of the two-dimensional images 38 to be produced, for example, in a sagittal plane or coronal plane). In modern medical imaging machines 20, the reconstruction engine 34 will have a large number of imaging parameters 40 describing numerous choices in the reconstruction process.

Generally the imaging parameters 40 include parameters that primarily affect only the acquisition of the data, parameters that are directed solely to reconstruction of the acquired data, and parameters with respect image processing that can be performed after reconstruction.

As an example, in a CT machine, the imaging parameters 40 may include acquisition centered parameters such as those describing x-ray collimator settings, tube voltage, xray filtration (i.e. spectral filtration), scanning speed, gating, a gantry angle of the gantry holding the x-ray tube and sensors for rotation, and the use of dual energy x-rays. The reconstruction centered parameters include number of images produced, MIP settings, slice data filtration, orientation of images, dual energy reconstruction (material base pair selection), window width and level, series description. Many acquisition centered parameters are interactive with reconstruction centered parameters making it difficult to separate them. For example, the use of dual energy in acquisition and the use of a dual energy reconstruction, and the use of gating during acquisition and handling that gating during reconstruction.

Importantly, modification of the image with respect to many of the imaging parameters 40 normally requires access to the reconstruction engine 34 of the particular medical imaging machine 20.

Medical imaging machines 20 having different modalities will have different imaging parameters 40. Even among a particular modality of medical imaging machine 20, the imaging parameters 40 will differ. In any given scan of a patient, the settings of the imaging parameters 40 will also differ among operators and according to different diagnostic indications and the preference of physicians.

The present invention provides each of the medical imaging machines 20 with a set of "high information imaging parameters" 40' that may differ substantially from normal diagnostic imaging parameters 40 in that they provide high information content volumetric (HICV) data 36'. HICV data 36' is obtained instead of the data normally provided by the reconstruction engine for diagnostic purposes which has lower information content.

The HICV data 36' can be obtained by selecting imaging parameters 40' that provide very high resolution (thin slices) and very low filtration. In most cases, this HICV data 36' provides the very highest resolution possible by the medical imaging device 20 with no filtration and with no other processing, for example, segmentation or MIP. Filtration generally refers to any process that reduces the information content of the volumetric data by the combination of underlying acquisition data or volumetric data, for example, in the latter case by increasing slice thickness or providing spatial filtration across slices. The combining may be according to an averaging or convolution process with a kernel or Gaussian blurring or other filtration process well known in the art or may be a side effect of other imaging parameters. As will be understood from the description herein, higher information content image data can be manipulated to produce lower information content image data but the reverse is not true. Filtration processes "window" or truncate Fourier coefficients of the acquisition data and/or the resulting volumetric or image data to improve apparent signal-to-noise ratio or diagnostic quality. The HICV data 36' will also be obtained with imaging parameters such as maximum intensity projection processing and image segmentation turned off such as would substantially reduce the information content of the data irreversibly.

In practice, special reconstructions may not be needed to generate HICV data. Some clinical indications already require minimally filtered data that may be appropriate for use as HICV data. For example, the invention being described here may be realized using thin slice thickness, high resolution images designed for diagnosing lung parenchyma issues to generate thicker slice thickness lower resolution images for diagnosing the mediastinum and for generating MIP images of the lung fields. This example is for chest imaging in CT, but other examples exist for other indication within CT and other modalities and may serve for HICV data generation.

It will be appreciated that the HICV data 36' need not be a single data set or even necessarily a contiguous volume of data. In some cases a medical imaging machine 20 will provide improved information content with smaller fields of view, for example, a field-of-view encompassing only the spine of a patient versus the entire chest cavity. In this case, the HICV data 36' may optionally be provided to linked sets of volumetric data that overlap with one set providing a subset at higher resolution. In another example, the HICV data 36' may include one or more small regions of interest together with a larger volume covering the entire exam at the scan field of view used for the final images. Alternatively, the HICV data 36' may include two identical or separated regions having different acquisition parameters or may include two distinct locations in the body.

Referring still to FIG. 1, the network interface 19 may also communicate with one or more display terminals 41 providing generally computer monitors and local computers connectable to the network to receive data for images 38 and display of that image data, for example, per terminals for implementing portions of a picture archiving and communication system (PACS). The images produced by the present invention will be desirably compatible with such display terminals 41.

The database 18 of the present invention, which may be implemented using a database program in memory 16 working with the processor 14 and mass storage devices of the server 12 will generally hold different sets of HICV data 36' collected using the parameters 40' discussed above. As is understood in the art, this volumetric data 36 may be stored using the DICOM (Digital Imaging and Communications in Medicine) for simplicity and compatibility although the invention contemplates that other standards or proprietary systems may be used for this data. The HICV data 36' will be associated with metadata 42, for example, describing some or all of the high information imaging parameters 40 used for the data acquisition as well as identification of the patient, the region of interest, and the use of contrast medium. In addition, the metadata 42 may provide a unique identification of the medical imaging device 20 from which the data is obtained.

The database 18 of the presentation server 12 may also include image set 39 from a particular medical imaging machine 20 that may, for example, be linked with particular HICV data 36' also obtained from that medical imaging machine 20 for use in compensating for machine-to-machine variations as will be discussed below. This image set 39 may also have metadata 44 inheriting the metadata 42 of the underlying HICV data 36' as well as an identification of that underlying HICV data 36' and further including orientation of the images 38 of the image set 39 and possibly the starting and ending location of the image sequence. The image set 39 may be matched to corresponding HICV data 36' using the metadata 42 and 44 to create a linking, for example, by common identification numbers. The metadata 44 may also include in some cases a template 54 used to generate the image set 39 from the HICV data 36'. The invention also contemplates storage of another information image set 39' natively obtained from a medical imaging machine 20 directly. This image set 39' will also have similar metadata. 44 but without template information and without identification of underlying HICV data 36'.

The memory 16 of the presentation server 12 may include an image modification program 50 which will be discussed in greater detail below and which provides for the generation of images 38 from the HICV data 36' and in DICOM form to be sent to the display terminals 41 for diagnosis. The image modification program 50 may be guided by image format parameters optionally stored in one or more templates 54. Individual templates may be associated with particular physicians (representing his or her preference for image display) and/or particular indications (e.g., head scan, liver scan etc.).

The memory 16 may also include a physician/procedure template-generating program 56 that may be executed by the processor 14 to these templates and a conversion template-generating program 58 executable by the processor 14 to generate templates that manage machine-to-machine differences discussed above and in more detail below. The memory 16 may further include a harmonization program 62 for harmonizing pairs of images for improved comparison and also to be discussed below.

The presentation server 12 may be located arbitrarily with respect to the display terminals 21 and the medical imaging machines 20, for example, being incorporated in either or centrally located as a server connected to a network. Preferably, the presentation server 12 is centrally located to serve as a repository for multiple computer imaging machines 20 and display terminals 21. The presentation server 12 may include other features associated with servers and processors including a display terminal, keyboard, and the like.

Figure 2:
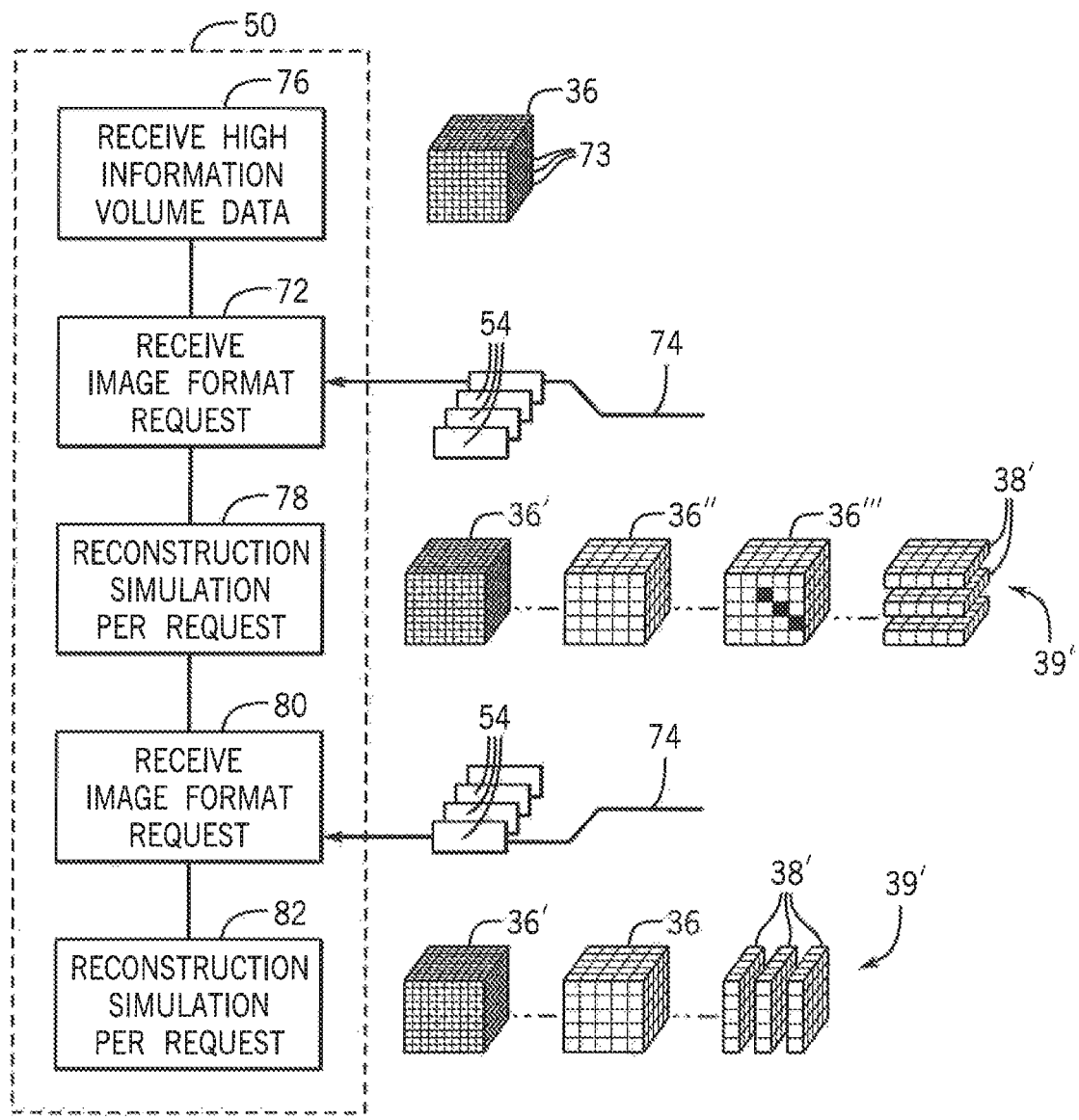
FIG. 2 is a flowchart of the image modification program of FIG. 1 with process blocks of the flowchart positioned near representations of the data being manipulated.

Referring now to FIG. 2, the image modification program 50 may operate as indicated by process block 72 to receive HICV data 36' composed of multiple voxel elements 73 each associated with a spatially corresponding volume element within patient tissue and describing a value characterizing that volume element dependent on the image modality of the medical imaging machine 20 as discussed above.

At process block 72, the image modification program 50 may receive an image format request 74 providing a set of image format parameters or identifying a template 54 holding a set of image format parameters associated with a particular physician or procedure. These image format parameters allow the HICV data 36' to be processed to match a type of image normally produced by the reconstruction engine of the medical imaging device 20 for diagnostic purposes. The present inventor has determined that many types of diagnostic images can be obtained from HICV data 36' through relatively simple manipulation without duplicating the reconstruction process or requiring access to the medical imaging device 20 on which the original reconstruction was performed. Specifically, the image format parameters used to adjust a degree of filtration of the HICV data 36' may change the image slice thickness of resultant images 38, may change the orientation of the images 38 obtained from the HICV data 36', may change the window width or level, may change the series description and may implement a wide variety of other image data manipulations frequently done in the reconstruction engine but technically independent from the reconstruction including maximum intensity projection processing (MIP) and image segmentation, coronary fractional flow reserve calculations, perfusion maps, volume renderings, organ volumes, distance measurements (i.e. for stent or valve placements), bone mineral density images, functional images (i.e. perfusion parameters).

In maximum intensity projection processing, the maximum intensity voxels in a volume are projected into the plane of the resulting image 38. In image segmentation, boundaries are established within the volumetric data (for example, defining a perimeter of an organ or chamber) to eliminate or modify some data not within the boundary.

As illustrated by process block 78, reconstruction using the image format parameters is then simulated using the HICV data 36'. For example, filtration or image thickness adjustment may be done by combining the values of adjacent voxels to produce filtered or thick-slice volumetric data 36'' simulating the data that would be reconstructed if these parameters were provided to the reconstruction engine. The combination process may be a simple averaging or weighted averaging or may make use of convolution with a kernel such as a Gaussian kernel or the like. Selecting the proper filtering to be applied to the HICV data 36' to produce an image similar to that produced by the reconstruction engine will be discussed below.

The HICV data 36' may be further processed to provide a variety of other image characteristics normally implemented by the reconstruction engine including MIP and segmentation to produce further processed lower information content data 36'''. This processing may use standard algorithms operating directly on the HICV data 36'. Finally, the orientation of the images 38 may be selected, for example, as a set of sagittal or coronal slices, by properly sequencing through the lower information content data 36''' to produce an image set 39' of 2D reconstructed HICV-derived images 38' simulating those that would be to produce by the reconstruction engine. It will be appreciated that other planes can be established by interpolation along diagonals to the columns and rows of the lower information content data 36'''.

This ability to select the orientation of the images 38 after reconstruction is particularly valuable because it allows data originally acquired, for example, in a sagittal plane for a particular purpose to be later reused for diagnosis that requires a coronal plane or the like without the need for additional scanning of the patient.

While the processing of process block 78 allows for simulation of processing that can be done by the reconstruction engine, the importance of the present invention is that the HICV data 36' is not tied to the particular HICV-derived images 38' produced but may be reused to produce images according to a different preference (of a different physician) or different diagnostic purpose in a different way according to a different radiologist's preference or for a different indication. In this regard, at process block 80, a new image format request 74 may be received, for example, using a different template 54 which may have different image processing parameters. At process block 82, the same stored HICV data 36' may then be processed in a different way, for example, with different filtration to produce thick slice volumetric data 36" and, given a different orientation, to produce an image set 39' of reconstructed HICV-derived images 38'. This reuse of the HICV data 36' may be repeated indefinitely so different radiologists can make use of this data in different ways with a different filtration action engine of the medical imaging device 20 accessed.

Figure 5:
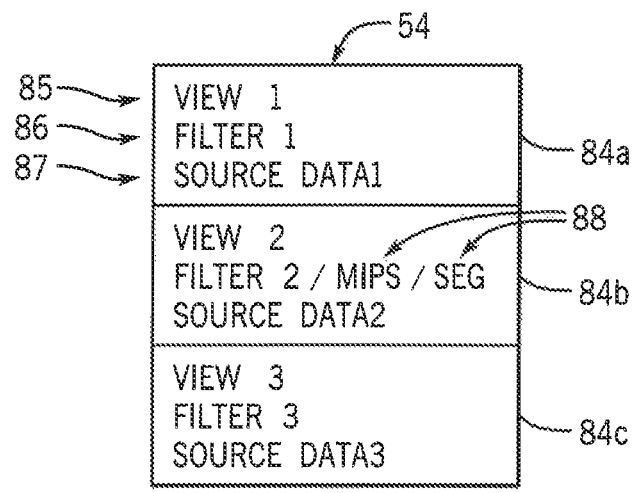
FIG. 5 is an example template for image modification using the image modification program of FIG. 1.

Referring now to FIG. 5, a given template 54 may describe desired image format parameters for a set of different image collections 84a-84c. Each image collection 84 may provide for a set or stack of reconstructed HICV-derived images 38' having different reconstruction requirements including different orientations 85 and different filtering 86 or other lossy processing 88.

Figure 3:
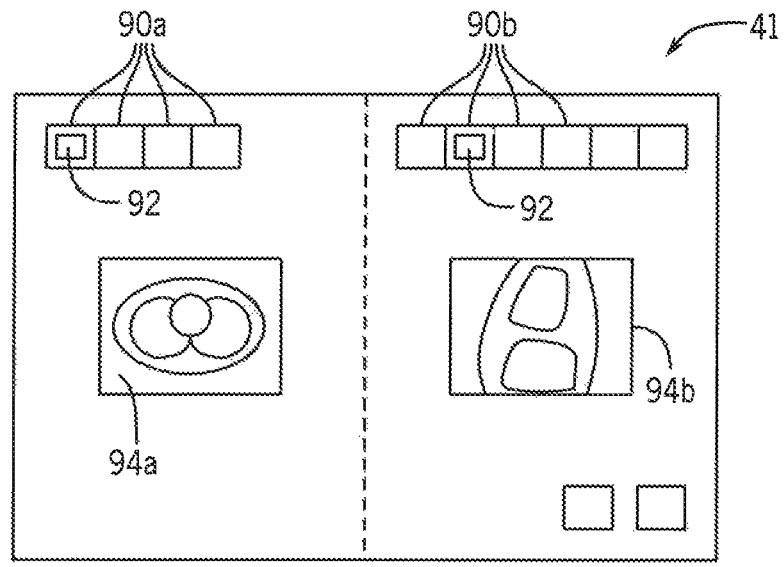
FIG. 3 is a screenshot of a display station of FIG. 1 showing two image sequences requiring comparison but before harmonization per the present invention.
Figure 4:
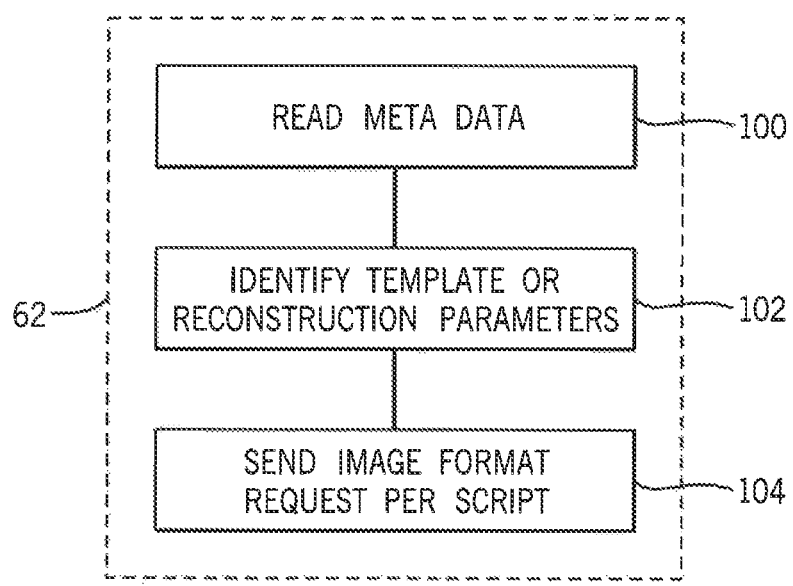
FIG. 4 is a flowchart of a harmonizing program executed by the central presentation server for harmonizing the images of FIG. 3 using a machine specific script.

Referring now to FIG. 3 as well as to FIGS. 1 and 2, the processing of the HICV data 36' discussed above can be used to harmonize images of different data sets. For example, during a longitudinal observation of a patient, a first set of images 90a may be prepared and selected from a set of thumbnails where a given highlighted image 92 may be displayed in large format 94a as shown. This first set of images 90a may have a filtration and/or orientation selected by a first physician or machine operator for display on the display terminals 21 A later acquisition of data from the same patient may produce a second set of images 90b having different filtration and/or orientation preferred by the reviewing radiologist. The radiologist desiring similar sets of images 90a and 90b may invoke the image harmonization program 62 (of FIG. 1) implementing the steps shown in FIG. 4.

At a first process block 100 of the metadata 44 of the underlying HICV data 36', the set of images 90b (shown on the right side of FIG. 3) may be read. In addition the metadata 44 for the images 38 of the set of images 90a is read.

At process block 102, the presentation server 12 uses the metadata 44 for the sets of images 90a and 90b to determine the underlying associated HICV data 36' files for the sets of images 90a and 90b and to identify a template 54 used in generating the desired sets of images 90b.

At process block 104, the presentation server 12 uses the identified template 54 for the set of images 90b and applies it to the HICV data 36' underlying the set of images 90a to convert that set of images 90a into a set of images matching the set of images 90b in terms of the number of images, their orientations, slice thicknesses, and filtration. This new set of images 90a uses the processes of process block 72 and 78 (or 80 of 82) of FIG. 2 to harmonize the set of images 90a into a visually similar set of images 90a facilitating the comparison of the different underlying data. Alternatively, the reviewing radiologist may request processing of the underlying HICV data 36' for each of the sets of images 90a and 90b under a new common set of image format parameters or different but common templates 54 nevertheless yielding comparable images.

It will be appreciated that the set of images 90a may include images 38 not prepared from HICV data 36' but, for example, obtained directly from the reconstruction engine of a medical imaging machine 20. In this case there may be no underlying HICV data 36', and accordingly a new set of images 90a cannot be generated per the approach discussed above. In this case, the reviewing physician may elect to transform the set of images 90b to match the set of images 90a by reformatting the HICV data 36' underlying the set of images 90b. This reformatting may be performed by manual entry of image format parameters or may be automatic by review of the normal DICOM metadata (header) of images of the set of images 90a to automatically extract necessary image format parameters for modification of the set of images 90b. For this purpose, the present invention contemplates conversion templates 54 that translate imaging parameters of DICOM header information into image format parameters for processing HICV data 36'.

Figure 7:
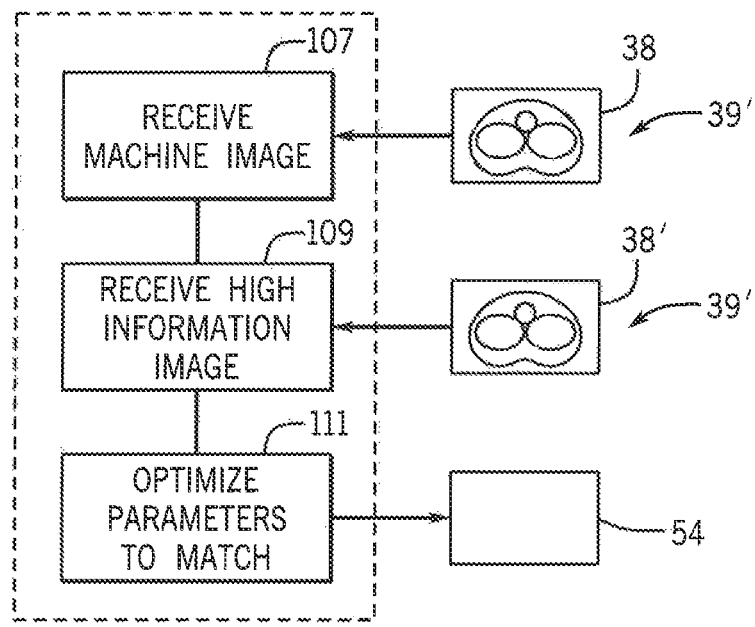
FIG. 7 is a script generating program executed by the central presentation server for generating scripts used by a program of FIG. 4.

Referring now to FIG. 7, a first step in developing a conversion template 54 obtains standard reconstructed images 38 obtained directly from the reconstruction engine of a medical imaging machine 20 as indicated by process block 107. At process block 109, the same acquisition data is used by the reconstruction engine of the same medical imaging machine 20 to develop corresponding HICV data 36'. At process block 111, an iterative process is used to adjust the image processing parameters for the HICV data 36' to maximize the similarity (e.g. correlation or the like) between the received image 38 and an image 38' produced from HICV data 36'. This iterative process may use standard hill climbing or other matching techniques. In this case, the orientation of the image 38 and reconstructed HICV images 38' is set to be identical and no processing other than filtering is used. When an optimum match is obtained, the image format parameters used for that match become a conversion template 54 usable in the process of FIG. 4 that can be applied to HICV data 36'.

Alternatively, it will be appreciated that the image 38 may be analyzed directly to characterize it with respect to image quality (IQ) capturing parameters like noise, entropy, information content and the like. These extracted parameters may be used to modify the HICV data 36' either iteratively or according to preprepared templates that map the extracted parameters to image format parameters for the program 50. Techniques for measuring image quality from images are described for example at Malkus, Annelise, and Timothy P. Szczykutowicz. "A method to extract image noise level from patient images in CT." Medical physics 44.6 (2017): 2173-2184; Tian, Xiaoyu, and Ehsan Samei. "Accurate assessment and prediction of noise in clinical CT images." Medical physics 43.1 (2016): 475-482; and Sanders, Jeremiah, Lynne Hurwitz, and Ehsan Samei. "Patient-specific quantification of image quality; an automated method for measuring spatial resolution in clinical CT images." Medical physics 43.10 (2016): 5330-5338.

Figure 6:
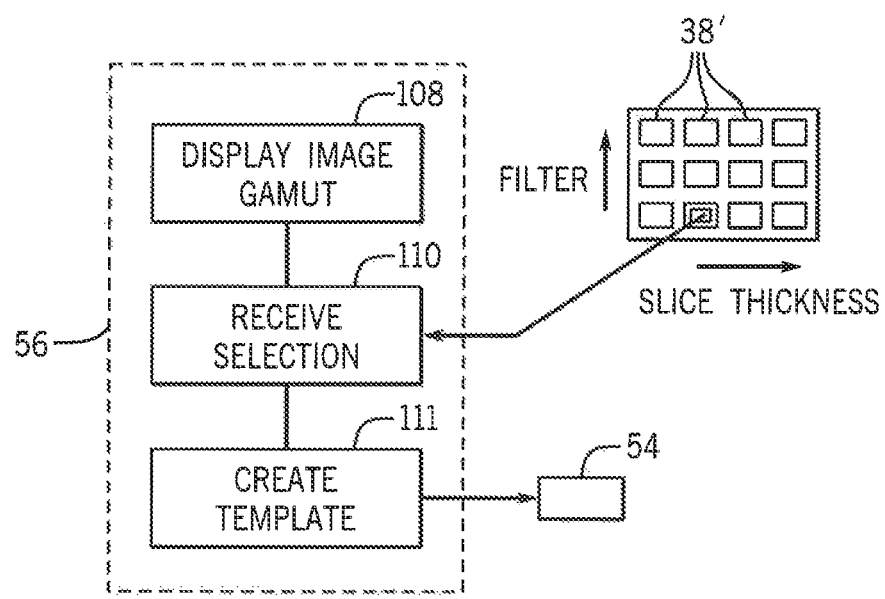
FIG. 6 is a template-generation program executed by the central presentation server for generating templates of FIG. 5.

Development of the physician/procedure templates 54 discussed above with respect to FIG. 4 may be done somewhat differently by a physician/procedure template-generating program 56. As shown in FIG. 6, at a first step in the physician/procedure template-generating program 56, indicated by process block 108, given HICV data 36' is processed using a range of different image format parameters, for example, stepping through filtration values and slice thickness values, to produce multiple reconstructed HICV images 38' in a grid. Per process block 110, the physician may review this grid of images 38' to select the desired image for diagnosis. Once a selection is made and received, at process block 110 the particular filtration slice thicknesses are stored to create a template at process block 111.

Alternatively, the physician/procedure templates 54 may be created manually by the radiologist entering the necessary parameters into a template editor or by selecting imaging parameters which are converted using conversion templates 54 discussed above.

Figure 8:
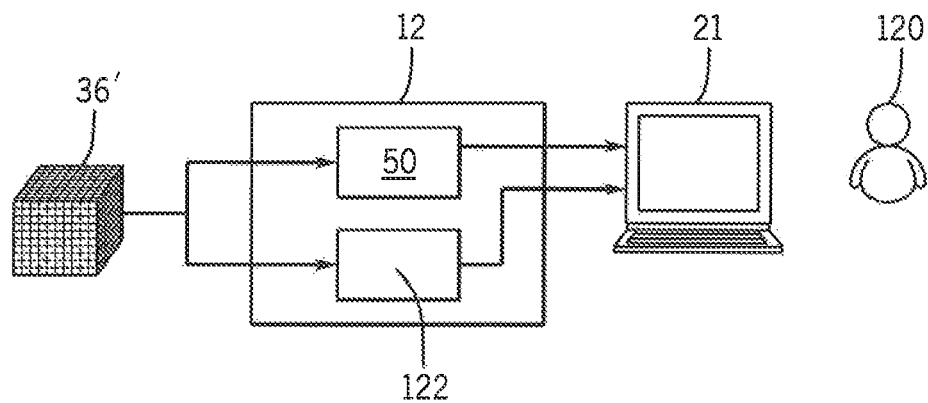
FIG. 8 is a data flow diagram showing use of the HICV storage format to provide improved machine analysis of data free from lossy processing for human readability.

Referring now to FIG. 8, an important benefit to the generation and storage of HICV data 36' is that it allows processing by program 50 for the purpose of presenting the data to a diagnostician 120, such as may introduce loss in the data for the purpose of improving the data readability to a clinician, while simultaneously providing the maximum data content for processing by machine vision systems 122, for example, those using supervised machine learning which do not require the processing steps of program 50 which are idiosyncratic to human vision and diagnosis. Generally, the machine vision system 122 may use any number of different machine learning approaches including supervised or unsupervised learning, artificial neural networks and the like. Generally, the machine vision system 122 will be trained using a training set having HICV data 36' associated with particular clinical indications. After training the machine vision system 122 can receive new HICV data 36' to provide a clinical indication to the diagnostician 120. The invention thus is future-looking to preserve data in a way that will augment cooperative diagnosis by humans and machines using artificial intelligence and the like. The image by the program 50 and diagnostic information from the machine vision system 122 (which may be presented as an image or as quantitative data or the like) may both be presented to the diagnostician 120 on display terminal 21.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted, it is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What I claim is:

1. A medical image processing system for data acquired from a medical imaging device collecting acquisition data from patients that is reconstructed to provide volumetric data, the medical image processing system comprising:
   a network interface communicating with multiple medical imaging machines having reconstruction engines;
   a memory system storing high information content volumetric (HICV) data received over the network interface from multiple medical imaging devices after reconstruction of acquisition data acquired by the multiple medical imaging devices on the multiple medical imaging devices; and
   a presentation processor communicating with the memory system and including an electronic computer executing a program stored in non-transitory media to:
   (a) receive first and second image format requests for volumetric data from a given medical imaging device, the requests identifying format parameters for reformatting of the HICV data;
   (b) process given HICV data from the memory system corresponding to the volumetric data according to the first image format request to provide and display a first set of images having a first slice orientation and/or first spatial filtration; and
   (c) process the given HICV data from the memory system according to the second image format request to provide and display a second set of images having a second slice orientation and/or second spatial filtration where at least one of the first and second slice orientations or at least one of the first and second spatial filtrations differ;

whereby different image presentations can be made without repeated reconstruction of the acquisition data.

2. The medical image processing system of claim 1 wherein the HICV data is data obtained from the medical imaging devices using imaging parameters minimizing filtration of the volumetric data.

3. The medical image processing system of claim 1 wherein the HICV data is obtained from the medical imaging devices using a highest resolution of the medical imaging devices.

4. The medical image processing system of claim 3 wherein the HICV data is obtained from the medical imaging devices using imaging parameters that maximize the information content of HICV data.

5. The medical image processing system of claim 1 wherein the HICV data is obtained from a medical imaging machine before windowing of Fourier data underlying the HICV data.

6. The medical image processing system of claim 1 wherein the HICV data employs a reconstruction having parameters that disable maximum intensity projection processing and image segmentation.

7. The medical image processing system of claim 1 wherein the image format requests identify among multiple templates stored in the memory system, the templates describing the processing of the HICV data to produce a set of images according to an image format request.

8. The medical image processing system of claim 7 wherein the multiple templates further specify maximum intensity projections and/or image segmentation operations.

9. The medical image processing system of claim 1 wherein the presentation processor includes a network interface for communicating with at least one display terminal for displaying human readable images to a healthcare professional; and wherein the electronic computer further executes to communicate with a healthcare professional at a display terminal by providing human readable images and receiving commands through the display terminal from the healthcare professional to modify the processing of the given HICV data.

10. The medical image processing system of claim 1 wherein the presentation processor includes a network interface for communicating with at least one display terminal for displaying images to a healthcare professional and further including the step of:
(d) transmitting the first set of images and the second set of images over the network to at least one display terminal.

11. The medical image processing system of claim 1 wherein the given HICV data includes first and second volumetric data having a differences selected from the group consisting of: different regions of the body and different acquisition parameters.

12. The medical image processing system of claim 1 wherein the devices are selected from the group consisting of CT, MRI, PET, and SPECT imaging machines.

13. The medical image processing system of claim 1 wherein the electronic computer further executes the program to process the HICV data directly using machine learning in which the HICV is processed by a program trained using a training set of HICV data and clinical conditions to provide an output indicating a clinical condition.

14. A medical image processing system for data acquired from a medical imaging device collecting acquisition data from patients that is reconstructed to provide volumetric data, the medical image processing system comprising:
a memory system storing high information content volumetric (HICV) data from multiple medical imaging devices after reconstruction of acquisition data acquired by the multiple medical imaging devices; and
a presentation processor communicating with the memory system and including an electronic computer executing a program stored in non-transitory media to:
(a) receive first and second image format requests for volumetric data from a given medical imaging device;
(b) process HICV data corresponding to the volumetric data to provide a first set of images having a first slice orientation and/or first spatial filtration; and
(c) process the HICV data to provide a second set of images having a second slice orientation and/or second spatial filtration where at least one of the first and second slice orientations or at least one of the first and second spatial filtrations differ;
whereby different image presentations can be made without repeated reconstruction of the acquisition data wherein the HICV data includes metadata identifying a medical imaging device and wherein the image format request identifies a script associated with a medical imaging device providing the HICV data, the script providing additional filtration information.

15. The medical image processing system of claim 14 wherein the memory system further stores at least one given machine image corresponding to the given HICV data but produced by the medical imaging device in a reconstruction different from the reconstruction producing the given HICV data; and
wherein the presentation processor develops a script by determining a processing of the given HICV data that produces images matching the given machine image, that processing defining the script.

16. A medical image processing system for data acquired from a medical imaging device collecting acquisition data from patients that is reconstructed to provide volumetric data, the medical image processing system comprising:
a memory system storing high information content volumetric (HICV) data from multiple medical imaging devices after reconstruction of acquisition data acquired by the multiple medical imaging devices; and
a presentation processor communicating with the memory system and including an electronic computer executing a program stored in non-transitory media to:
(a) receive first and second image format requests for volumetric data from a given medical imaging device;
(b) process HICV data corresponding to the volumetric data to provide a first set of images having a first slice orientation and/or first spatial filtration; and
(c) process the HICV data to provide a second set of images having a second slice orientation and/or second spatial filtration where at least one of the first and second slice orientations or at least one of the first and second spatial filtrations differ;
whereby different image presentations can be made without repeated reconstruction of the acquisition data
wherein the presentation processor includes a network interface for communicating with at least one display terminal for displaying images to a healthcare professional and wherein the electronic computer further executes the program to:

(d) process second HICV data to provide a third set of images having a third slice orientation and/or third spatial filtration;
(e) receive a command from a display terminal identifying the first set of images and a request to match the first set of images and third set of images; and
(f) processes the second HICV data a according to the processing of the given HICV data used to produce the first set of images to provide a fourth set of images and transmit the fourth set of images to the display terminal.

17. A medical image processing system for data acquired from a medical imaging device collecting acquisition data from patients that is reconstructed to provide volumetric data, the medical image processing system comprising:
a memory system storing high information content volumetric (HICV) data from multiple medical imaging devices after reconstruction of acquisition data acquired by the multiple medical imaging devices; and
a presentation processor communicating with the memory system and including an electronic computer executing a program stored in non-transitory media to:
(a) receive first and second image format requests for volumetric data from a given medical imaging device;
(b) process HICV data corresponding to the volumetric data to provide a first set of images having a first slice orientation and/or first spatial filtration; and
(c) process the HICV data to provide a second set of images having a second slice orientation and/or second spatial filtration where at least one of the first and second slice orientations or at least one of the first and second spatial filtrations differ;
whereby different image presentations can be made without repeated reconstruction of the acquisition data
wherein the presentation processor includes a network interface for communicating with at least one display terminal for displaying images to a healthcare professional and wherein the electronic computer further executes the program to:
(d) receive a third set of images not obtained from HICV data having a third slice orientation and/or third spatial filtration;
(e) receive a command from a display terminal to match the first set of images to the third set of images; and
(f) process the given HICV data to provide a fourth set of images to have a third slice orientation and/or third spatial filtration and transmit the third set of images and fourth set of images to the display terminal.

18. The medical image processing system of claim 17 wherein the third set of images not obtained from HICV data includes metadata describing the third slice orientation and/or third spatial filtration and the step (f) reads the metadata to provide the processing of the given HICV data to provide the fourth set of images.

* * * * *